US008983255B2

(12) United States Patent
Shinji et al.

(10) Patent No.: US 8,983,255 B2
(45) Date of Patent: Mar. 17, 2015

(54) COMPOSITE OPTICAL FIBER AND METHOD OF MANUFACTURING THE SAME

(75) Inventors: Osamu Shinji, Tainai (JP); Katashi Saito, Tainai (JP); Kiyoshi Oka, Mito (JP)

(73) Assignees: Kuraray Co., Ltd., Kurashiki-shi (JP); Japan Atomic Energy Agency, Naka-gun (JP)

( * ) Notice: Subject to any disclaimer, the term of this patent is extended or adjusted under 35 U.S.C. 154(b) by 112 days.

(21) Appl. No.: 13/701,976

(22) PCT Filed: Jun. 6, 2011

(86) PCT No.: PCT/JP2011/062939
§ 371 (c)(1),
(2), (4) Date: Feb. 19, 2013

(87) PCT Pub. No.: WO2011/155444
PCT Pub. Date: Dec. 15, 2011

(65) Prior Publication Data
US 2013/0156389 A1    Jun. 20, 2013

(30) Foreign Application Priority Data
Jun. 8, 2010    (JP) .................................. 2010-131176

(51) Int. Cl.
*G02B 6/44*    (2006.01)
*A61B 1/00*    (2006.01)
(Continued)

(52) U.S. Cl.
CPC .......... *G02B 6/4486* (2013.01); *A61B 1/00167* (2013.01); *A61B 1/07* (2013.01);
(Continued)

(58) Field of Classification Search
CPC .................................... G02B 6/04; G02B 1/00
USPC ................................................. 385/100–113
See application file for complete search history.

(56) References Cited

U.S. PATENT DOCUMENTS

| 4,896,941 A | * | 1/1990 | Hayashi et al. | ............... 385/116 |
| 5,881,195 A | * | 3/1999 | Walker | .......................... 385/116 |

(Continued)

FOREIGN PATENT DOCUMENTS

| JP | 6 186445 | 7/1994 |
| JP | 6 265735 | 9/1994 |

(Continued)

OTHER PUBLICATIONS

International Search Report Issued Jun. 28, 2011 in PCT/JP11/62939 Filed Jun. 6, 2011.

*Primary Examiner* — Eric Wong
(74) *Attorney, Agent, or Firm* — Oblon, McClelland, Maier & Neustadt, L.L.P.

(57) ABSTRACT

Disclosed is a composite optical fiber which has high flexibility and is hard to break. The composite optical fiber comprises a larger-diameter optical fiber and smaller-diameter optical fibers each having a smaller diameter than that of the larger-diameter optical fiber, wherein the larger-diameter fiber and the smaller-diameter optical fibers are so arranged that the larger-diameter fiber is surrounded by the smaller-diameter optical fibers, and the smaller-diameter optical fibers that surround the larger-diameter optical fiber are made from a plastic material.

19 Claims, 5 Drawing Sheets

(51) Int. Cl.

| | | |
|---|---|---|
| *A61B 1/07* | (2006.01) | |
| *G02B 6/02* | (2006.01) | |
| *G02B 23/24* | (2006.01) | |
| *G02B 23/26* | (2006.01) | |
| *G02B 6/06* | (2006.01) | |

(52) U.S. Cl.
CPC ........ *G02B 6/02333* (2013.01); *G02B 6/02347* (2013.01); *G02B 23/2469* (2013.01); *G02B 23/26* (2013.01); *G02B 6/06* (2013.01); *A61B 1/0017* (2013.01); *A61B 1/0011* (2013.01); *G02B 6/02033* (2013.01)
USPC ........................................................ 385/109

(56) References Cited

U.S. PATENT DOCUMENTS

| | | | |
|---|---|---|---|
| 2005/0192480 A1* | 9/2005 | Toriya et al. ................... | 600/182 |
| 2006/0165358 A1* | 7/2006 | Trebst et al. .................. | 385/115 |
| 2006/0190006 A1 | 8/2006 | Oka et al. | |
| 2010/0163537 A1 | 7/2010 | Furuta et al. | |

FOREIGN PATENT DOCUMENTS

| | | |
|---|---|---|
| JP | 9 216086 | 8/1997 |
| JP | 2005 237436 | 9/2005 |
| JP | 2006 58740 | 3/2006 |
| JP | 2006 223710 | 8/2006 |
| WO | 2008 123609 | 10/2008 |

* cited by examiner

COMPOSITE OPTICAL FIBER AND METHOD OF MANUFACTURING THE SAME This application is a 371 of PCT/JP2011/062939 filed Jun. 6, 2011.

TECHNICAL FIELD

The present invention relates to a composite optical fiber.

BACKGROUND ART

In apparatuses for examination (visualization) for use in inspection of industrial products and/or medical examination, optical fiber-based image fibers are employed. The apparatuses of this type are mainly used in visualization (diagnosis) of internal defects inside products or diseased parts inside the body.

When making repairs on a welded portion within a pipe in an industrial product or giving therapy on the inside of a human body, laser light is employed. In guiding laser light to a target portion (for example, a welded portion in a pipe or a portion to be treated inside a human body), optical fibers are employed.

The internal visualization techniques using image fibers, and on the other hand, the repair/therapy techniques involving guiding laser light to the inside as described above, have developed independently of one another. In other words, these techniques are in totally different fields thus far.

Recently, for repair of a defect in piping or therapy of a diseased portion in a human body, a composite optical fiber has been proposed. The composite optical fiber is formed by combining, for example, an energy transmission fiber (energy transmission fiber for laser light) with image fibers (image fibers for visualization/examination). The energy transmission fiber is, for example, a large-diameter optical fiber. The image fiber is, for example, a small-diameter optical fiber having a diameter smaller than that of the large-diameter optical fiber. A large number of the small-diameter optical fibers (image fibers) are placed around a large-diameter optical fiber (an energy transmission fiber).

CITATION LIST

Patent Literature

PTL 1: JP P1997-216086A
PTL 2: JP P2006-223710A

SUMMARY OF INVENTION

Technical Problem

The composite optical fiber proposed thus far has high rigidity and is inflexible. For example, especially when used in medical applications, it is desirable to have bending flexibility such that the bending radius is of the order of 5 mm. Of course, such bending flexibility may also be required for optical fibers used in non-medical applications.

The composite optical fiber proposed thus far, however, does not satisfy the bending flexibility such that the bending radius is of the order of 5 mm.

Moreover, there are concerns about the composite optical fiber proposed thus far being easy to break.

Therefore, a problem to be solved by the present invention is to provide a composite optical fiber that has high bending flexibility and is hard to break.

Solution to Problem

To make a composite optical fiber have high bending flexibility, the diameter of the composite optical fiber may be reduced.

Consider a case in which a composite optical fiber is used in a medical application, for example, a case in which a composite optical fiber is inserted in a catheter tube. In such a case, it is desired that the outer diameter of the composite optical fiber is 1.5 mm or smaller including light guiding fibers and an outer jacket. Particularly, it is desired that the outer diameter is 1 mm or smaller. Then, a composite optical fiber is desired to have an outer diameter of about 1 mm or smaller excluding the light guiding fibers and outer jacket. When bending flexibility is regarded as of major importance, the outer diameter may be 0.5 mm or smaller.

It is, however, difficult to further reduce the outer diameter because of a problem of crosstalk or the like.

For the conventional composite optical fiber under such a condition, that is, that having an outer diameter of the order of 0.5 mm, it is difficult to satisfy bending flexibility such that the bending radius is of the order of 5 mm.

It turned out that the problem of bending flexibility of the composite optical fiber proposed thus far results from the fact that the base material of the composite optical fiber is inorganic glass such as quartz glass. Particularly, a large number of small-diameter optical fibers (image fibers) are installed around a large-diameter optical fiber (an energy transmission fiber). The small-diameter optical fibers (image fibers) are made of inorganic glass such as quartz glass. As a result, bending flexibility is significantly poor.

Of course, bending flexibility can be ensured by use of even an optical fiber made of inorganic glass insofar as it has a small outer diameter. However, there is a limit to reduction of the outer diameter of an optical fiber due to a problem of crosstalk or the like. For example, to obtain an image with high resolution by small-diameter optical fibers, a larger number of small-diameter optical fibers are required. A number of small-diameter optical fibers of, for example, 2,000 or more, are required. When placing 2,000 or more small-diameter optical fibers around a large-diameter optical fiber, there is a limit to the total size even though the diameter of a small-diameter optical fiber is reduced. A small-diameter optical fiber having too small a diameter causes a problem of crosstalk. A resulting image suffers from blurring. As such, the outer diameter of a composite optical fiber is limited to a size of the order of 0.4-0.5 mm thus far. Consequently, there still remains a problem in bending flexibility of the composite optical fiber proposed thus far.

A large number of inorganic glass small-diameter optical fibers placing around a large-diameter optical fiber pose a problem that bending flexibility is poor, and in addition, the fibers easily break when they are bent. The broken (fractured) fibers bring about concerns about compromised safety.

These concerns, however, can be eliminated by improving bending flexibility.

The present invention has been made based on the findings as described above.

Specifically, the aforementioned problem is solved by a composite optical fiber characterized in comprising:
a large-diameter optical fiber; and
small-diameter optical fibers each having a diameter smaller than that of said large-diameter optical fiber,
wherein said large-diameter optical fiber and said small-diameter optical fibers are placed such that said large-diameter optical fiber is surrounded by a group of a plurality of said small-diameter optical fibers, said small-diameter optical fibers are plastic optical fibers each comprising a core portion and a cladding portion, and said small-diameter optical fibers have their cladding portions welded to one another.

The aforementioned problem is also solved by the composite optical fiber described above characterized in that preferably, said large-diameter optical fiber has a diameter ranging from 30 μm to 300 μm, said small-diameter optical fiber has a core portion with a diameter ranging from 1 μm to 10 μm, and said composite optical fiber has an outer diameter ranging from 0.3 mm to 1.5 mm.

The aforementioned problem is also solved by the composite optical fiber described above characterized in that the number of said small-diameter optical fibers preferably ranges from 2,000 to 50,000.

The aforementioned problem is also solved by the composite optical fiber described above characterized in that said large-diameter optical fiber is preferably made of plastic. Alternatively, the aforementioned problem is also solved by the composite optical fiber described above characterized in that said large-diameter optical fiber is made of inorganic glass. In case that the large-diameter optical fiber is made of inorganic glass, the aforementioned problem is also solved by the composite optical fiber described above characterized in that the large-diameter optical fiber made of inorganic glass is preferably provided on its outer periphery with an organic protective layer.

Moreover, the aforementioned problem is solved by a method of manufacturing a composite optical fiber, characterized in comprising:

an elemental plastic optical fiber installing step;

a rod body installing step;

a pressure-reducing step; and a drawing step, wherein said elemental plastic optical fiber installing step is a step in which a plurality of elemental plastic optical fibers, each of which comprises a core portion and a cladding portion, are installed between a plastic outer pipe and a plastic inner pipe, said rod body installing step is a step in which a core rod comprising a transparent portion that is an optical fiber's constituent element is installed inside of the plastic inner pipe, said pressure-reducing step is a step in which an air pressure between said plastic outer pipe and said plastic inner pipe is reduced, and said drawing step is a step in which members comprising the plastic outer pipe, elemental plastic optical fibers, plastic inner pipe and core rod obtained through said elemental plastic optical fiber installing step and said rod body installing step are heated and drawn, said step being achieved with a gap portion among said members placed under a reduced-pressure condition.

Further, the aforementioned problem is solved by a method of manufacturing a composite optical fiber, characterized in comprising:

an installing step;

a pressure-reducing step; and a drawing step, wherein said installing step is a step in which a core rod comprising a transparent portion that is an optical fiber's constituent element, and elemental plastic optical fibers, each of which comprises a core portion and a cladding portion, are installed inside of a plastic pipe such that a plurality of said elemental plastic optical fibers surround said core rod, said pressure-reducing step is a step in which an air pressure within said plastic pipe is reduced, and said drawing step is a step in which members comprising the plastic pipe, elemental plastic optical fibers and core rod obtained through said installing step are heated and drawn, said step being achieved with a gap portion among said members placed under a reduced-pressure condition.

Furthermore, the aforementioned problem is solved by a method of manufacturing a composite optical fiber, characterized in comprising:

an elemental plastic optical fiber installing step;

a plastic inner pipe installing step;

a pressure-reducing step;

a drawing step; and an optical fiber installing step, wherein said elemental plastic optical fiber installing step is a step in which a plurality of elemental plastic optical fibers, each of which comprises a core portion and a cladding portion, are installed inside of a plastic outer pipe, said plastic inner pipe installing step is a step in which a plastic inner pipe is installed to be generally centered within the plastic outer pipe, said pressure-reducing step is a step in which an air pressure between said plastic outer pipe and said plastic inner pipe is reduced, said drawing step is a step in which members comprising the plastic outer pipe, elemental plastic optical fibers and plastic inner pipe obtained through said elemental plastic optical fiber installing step and said plastic inner pipe installing step are heated and drawn, said step being achieved with a gap portion among said members placed under a reduced-pressure condition, and said optical fiber installing step is a step in which an optical fiber is installed in the plastic inner pipe after said drawing step.

Advantageous Effects of Invention

Comparing organic resins (for example, polymethylmethacrylate resins or polystyrene resins) with inorganic glass (for example, quartz glass), the Young's modulus of the former is of the order of ¹⁄₂₀ of that of the latter. Therefore, a plastic optical fiber has high bending flexibility and is easy to bend as compared with a quartz optical fiber. For example, even an optical fiber having an outer diameter of 0.5 mm may well have a bending radius of the order of 5 mm. Moreover, a risk of fracture is low.

A plastic optical fiber may be quite safely employed as a large-diameter optical fiber in the center position. It was even possible to employ a quartz glass optical fiber as the large-diameter optical fiber in the center position. However, it was necessary to employ always plastic small-diameter optical fibers installed around the large-diameter optical fiber, particularly, installed to form a multiplicity of layers, in view of bending flexibility. By fulfilling this requirement, bending flexibility was significantly improved as compared with conventional quartz glass composite optical fiber.

When plastic optical fibers are employed, it is easy to select raw materials (which have a difference of the refractive index between the core portion and cladding portion ranging from about 0.07 to 0.1). That is, plastic optical fibers having a difference of the refractive index between the core portion and cladding portion ranging from about 0.07 to 0.1 are easily available. The optical fibers having such characteristics and each having a small diameter are hard to induce crosstalk even if a large number of them are bundled. Therefore, according to the present invention, since a large difference of the refractive index could be attained by employing plastic optical fibers, the fibers each having a small diameter could be employed as the large number of bundled small-diameter optical fibers. Since their diameter is small, the number of small-diameter optical fibers serving as image fibers for imaging can be increased for the whole composite optical fibers having the same diameter, and the number of pixels is increased accordingly. Thus, resolution is also improved. For example, bending flexibility is still high even when the number of small-diameter optical fibers (number of pixels) is 2,000 or more.

For example, the optical fiber is very preferable as optical fiber in an endoscope system with which visualization and therapy can be achieved at the same time.

DESCRIPTION OF EMBODIMENTS

Figure 1:
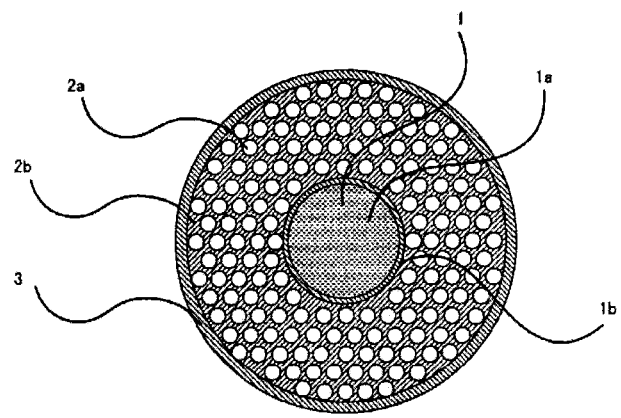
FIG. 1 A cross-sectional view of composite optical fiber in accordance with a first embodiment of the present invention.

A first aspect of the present invention is a composite optical fiber. The composite optical fiber comprises a large-diameter optical fiber and small-diameter optical fibers. The small-diameter optical fiber is an optical fiber having a diameter smaller than that of the large-diameter optical fiber. The large-diameter optical fiber enables laser light guiding. The small-diameter optical fibers enable image transmission. The large-diameter optical fiber and small-diameter optical fibers are installed such that the periphery (particularly, the whole periphery) of the large-diameter optical fiber is surrounded by a group of the small-diameter optical fibers. A number N (N is an integer equal to or more than two) of small-diameter optical fibers are employed. Preferably, 2,000-50,000 small-diameter optical fibers are installed surrounding the large-diameter optical fiber, for example. Particularly, the small-diameter optical fibers are installed to form a plurality of layers. The small-diameter optical fibers are particularly made of plastic.

In the composite optical fiber described above, the large-diameter optical fiber preferably had a diameter ranging from 30 µm to 300 µm. More preferably, the diameter was from 40 µm to 250 µm. Still more preferably, the diameter was from 50 µm to 200 µm. A reason why such a diameter was preferred was as follows: when the diameter was too small, as small as a diameter below 30 µm, it was difficult for laser light to be sufficiently focused and led into an end surface of the large-diameter optical fiber. From this point, the diameter of the core portion of the large-diameter optical fiber was more preferably 50 µm or more. On the contrary, when the diameter was too large, as large as a diameter above 300 µm, the proportion of the area of the image transmitting portion (small-diameter optical fibers) in the outer periphery was reduced, making image visualization difficult. It was also difficult to bend the fiber. The thickness of the cladding of the large-diameter optical fiber was preferably from 2 µm to 30 µm. When the thickness of the cladding was smaller than 2 µm, a phenomenon similar to crosstalk took place. Laser light easily leaked out of the fiber. Sometimes contrast of an image was degraded. On the contrary, when the thickness of the cladding exceeded 30 µm, the proportion of the core in the cross section of the large-diameter optical fiber was reduced. It was then difficult for laser light to be sufficiently focused and led into an end surface of the large-diameter optical fiber. The exterior of the cladding of the large-diameter optical fiber may be covered with an opaque covering member of a thickness ranging from 2 µm to 30 µm. In the composite optical fiber described above, the diameter of the core portion of the small-diameter optical fiber was preferably from 1 µm to 10 µm. More preferably, it was 2 µm or more. More preferably, it was 5 µm or less. A reason why such a diameter was preferred was as follows: when the diameter was too small, as small as a diameter below 1 µm, crosstalk took place. An image suffered from blurring. A resulting image was not bright due to an insufficient amount of light. On the contrary, when the diameter was too large, as large as a diameter above 10 µm, it was difficult to pack and install a large number of small-diameter optical fibers. When packing a large number of such fibers, the diameter of the composite optical fiber became larger. Consequently, flexural properties were degraded. In the composite optical fiber described above, the outer diameter of the composite optical fiber was preferably from 0.2 mm to 1.5 mm. More preferably, it was from 0.3 mm to 1.0 mm. Still more preferably, it was from 0.4 mm to 1.0 mm. A reason thereof was as follows: when the diameter is too small, as small as a diameter below 0.2 mm, the number of the small-diameter optical fibers is too small. As a result, the number of pixels is reduced. Resolution of a resulting image was reduced. On the contrary, when the diameter was too large, as large as a diameter above 1.5 mm, flexural properties were degraded. In the composite optical fiber described above, the number of plastic small-diameter optical fibers surrounding the large-diameter optical fiber was preferably from 2,000 to 50,000. More preferably, it was from 3,000 to 30,000. Still more preferably, it was from 5,000 to 20,000. A reason thereof was as follows: when the number was too small, as small as a number less than 2,000, resolution of a resulting image was reduced. When the number is too large, as large as a number greater than 50,000, flexural properties were degraded.

In the composite optical fiber described above, the plurality of plastic small-diameter optical fibers surrounding the large-diameter optical fiber have their cladding portions welded to one another. Because of the welded structure, an assembly of the small-diameter optical fibers has a cross section similar to a sea-island structure. Since the small-diameter optical fibers are made of plastic, their cladding portions of each fiber are welded/combined together by heating. Thus, the plurality of small-diameter optical fibers surrounding the large-diameter optical fiber are easily fixed together. That is, the small-diameter optical fibers are not easily displaced. Therefore, a resulting image had high quality.

In the composite optical fiber described above, the large-diameter optical fiber is preferably made of plastic. An example of the all-plastic composite optical fiber of this type is shown in FIG. 1. FIG. 1 is a cross-sectional view of composite optical fiber. In FIG. 1, a reference numeral 1 designates a large-diameter optical fiber. A reference numeral 1a designates a core portion (core portion guiding laser light), and 1b designates a cladding portion (cladding portion guiding laser light). The core portion 1a is constructed of a "rod body" in the manufacturing method described later. The cladding portion 1b is constructed of a "plastic inner pipe" in the manufacturing method described later. A reference numeral 2a designates a core portion of a small-diameter optical fiber (an image fiber). A reference numeral 2b designates a cladding portion. The core portion 2a and cladding portion 2b are constructed of an "elemental plastic optical fiber" in the manufacturing method described later. As described earlier, and as can be seen from FIG. 1, the cladding portions 2b are welded/combined together. That is, they form a sea-island structure (the core portions 2a correspond to islands and the cladding portion 2b corresponds to a sea). A reference numeral 3 designates outer cladding. It should be noted that the outer cladding 3 is not an absolutely necessary element. The outer cladding 3 is constructed of a "plastic outer pipe" in the manufacturing method described later.

Figure 4:
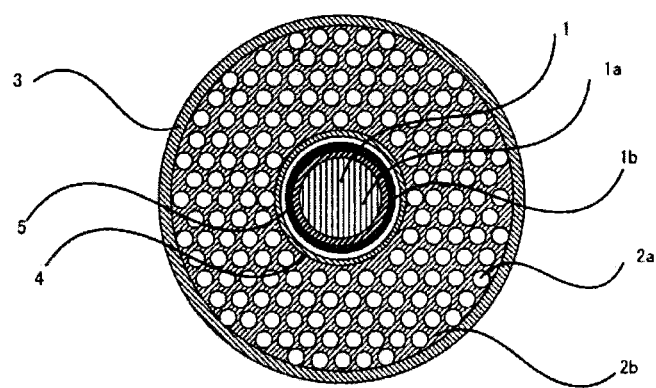
FIG. 4 A cross-sectional view of composite optical fiber in accordance with a second embodiment of the present invention.
Figure 5:
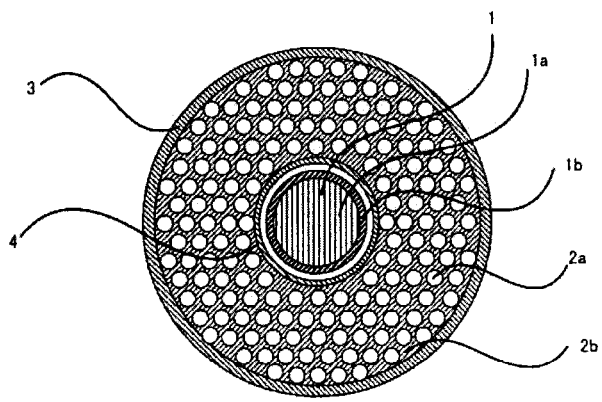
FIG. 5 A cross-sectional view of composite optical fiber in accordance with a third embodiment of the present invention.

The large-diameter optical fiber may be made of inorganic glass. When the large-diameter optical fiber is made of inorganic glass, the large-diameter optical fiber is preferably provided on its outer periphery with an organic resin layer (a protective layer). An example of the large-diameter optical fiber of this structure is shown in FIGS. 4, 5. FIGS. 4, 5 are cross-sectional views of composite optical fiber. FIG. 4 is one with an organic resin layer (protective layer) and FIG. 5 is one without an organic resin layer (protective layer). In FIGS. 4, 5, a reference numeral 1 designates a large-diameter optical fiber made of inorganic glass. A reference numeral 1a designates a core portion (core portion guiding laser light), and 1b designates a cladding portion (cladding portion guiding laser light). A reference numeral 2a designates a core portion of a small-diameter optical fiber (an image fiber). A reference numeral 2b designates a cladding portion. The core portion 2a and cladding portion 2b are constructed of an "elemental plastic optical fiber" in the manufacturing method described later. As described earlier, and as can be seen from FIGS. 4, 5, the cladding portions 2b are welded/combined together. That is, they form a sea-island structure (the core portions 2a correspond to islands and the cladding portion 2b corresponds to a sea). A reference numeral 3 designates outer cladding. A reference 4 designates inner cladding. It should be noted that the outer cladding 3 and inner cladding 4 are not absolutely necessary elements. The outer cladding 3 is constructed of a "plastic outer pipe" in the manufacturing method described later. The inner cladding 4 is constructed of a "plastic inner pipe" in the manufacturing method described later. A reference numeral 5 designates a sheathing layer for sheathing the large-diameter optical fiber 1 made of inorganic glass therein. The sheathing layer 5 improves resistance to break of the glass optical fiber 1. The sheathing layer 5 is preferably formed using, for example, silicone-based resins, UV-curable resins, polyimide-based resins, and the like. An electrically conductive metal sheath such as aluminum is employed as appropriate.

A second aspect of the present invention is a method of manufacturing a composite optical fiber. For example, it is a method of manufacturing the composite optical fiber described above.

The above-described manufacturing method has a step to install N elemental plastic optical fibers each comprising a core portion and a cladding portion between a plastic outer pipe and a plastic inner pipe. The plastic inner pipe corresponds to the cladding portion of the large-diameter fiber. The method also has a step to install a core rod comprising a transparent portion that is an optical fiber's constituent element inside of the plastic inner pipe. The core rod corresponds to the core portion of the large-diameter fiber. It should be noted that the core rod may be replaced with an optical fiber preform constituting a core and cladding. The method moreover has a pressure-reducing step of reducing the air pressure at least between the plastic outer pipe and plastic inner pipe. The method moreover has a drawing step of heating/drawing a gap portion among members comprising the plastic outer pipe, elemental plastic optical fibers, plastic inner pipe and core rod obtained through the elemental plastic optical fiber installing step and rod body installing step under a reduced-pressure condition. Since the drawing step is achieved under reduced-pressure and heated conditions, the elemental plastic optical fibers are welded/combined together at their peripheral portions. Moreover, since they are drawn under a reduced pressure, no gap is left. The assembly of the elemental plastic optical fibers has a cross section similar to a sea-island structure.

Alternatively, the above-described manufacturing method has an installing step of installing an optical fiber preform rod comprising a core and cladding inside of a plastic pipe, and N elemental plastic optical fibers each comprising a core portion and a cladding portion surrounding a periphery (particularly, the whole periphery) of the preform rod. This manufacturing method is different from the manufacturing method described above in that sometimes the plastic inner pipe as described above is not employed. The method also has a pressure-reducing step of reducing the air pressure within the plastic pipe. The method moreover has a drawing step of heating/drawing a gap portion among members comprising the plastic pipe, elemental plastic optical fibers and preform rod obtained through the installing step under a reduced-pressure condition. Since the drawing step is achieved under reduced-pressure and heated conditions, the elemental plastic optical fibers are welded/combined together at their peripheral portions. Moreover, since they are drawn under a reduced pressure, no gap is left. The assembly of the elemental plastic optical fibers has a cross section similar to a sea-island structure.

Alternatively, the above-described manufacturing method has an elemental plastic optical fiber installing step of installing N elemental plastic optical fibers each comprising a core portion and a cladding portion inside of a plastic outer pipe. The method also has a plastic inner pipe installing step of installing a plastic inner pipe to be generally centered within the plastic outer pipe. The method moreover has a pressure-reducing step of reducing the air pressure between the plastic outer pipe and plastic inner pipe. The method also has a drawing step of heating/drawing a gap portion among members comprising the plastic outer pipe, elemental plastic optical fibers and plastic inner pipe obtained through the elemental plastic optical fiber installing step and plastic inner pipe installing step under a reduced-pressure condition. Since the drawing step is achieved under reduced-pressure and heated conditions, the elemental plastic optical fibers are welded/combined together at their peripheral portions. Moreover, since they are drawn under a reduced pressure, no gap is left. The assembly of the elemental plastic optical fibers has a cross section similar to a sea-island structure.

Moreover, by drawing the elemental fibers without reducing the pressure of the center portion inward of the plastic inner pipe, the assembly of the small-diameter optical fibers is formed as a hollow optical fiber assembly having a penetrated hole around the center of the cross section.

By providing an optical fiber installing step of installing an optical fiber within the plastic inner pipe of the hollow optical fiber assembly, a composite optical fiber is obtained. By providing the plastic inner pipe installing step, the hollow optical fiber assembly and large-diameter optical fiber can be separately fabricated. Therefore, a material for the large-diameter optical fiber can be unrestrictedly selected, which is preferable in flexible production methods involving producing small batches of a variety of products. Moreover, since the hollow optical fiber assembly and large-diameter optical fiber are not welded/combined together, a resulting product has excellent flexibility. Since the drawing step is achieved under reduced-pressure and heated conditions, the elemental plastic optical fibers are welded/combined together at their peripheral portions. Moreover, since they are drawn under a reduced pressure, no gap is left. The assembly of the elemental plastic optical fibers has a cross section similar to a sea-island structure.

The diameter of the penetrated hole included through the hollow optical fiber assembly was preferably larger than the diameter of the large-diameter optical fiber including the covering member by a range from 5 μm to 100 μm. A range smaller than 5 μm makes the process difficult when fabricating the hollow optical fiber assembly beforehand and thereafter inserting the large-diameter optical fiber therein. On the other hand, a range greater than 100 μm makes no dramatic improvement on easiness of the aforementioned process, or rather, undesirably causes the area of the group of the small-diameter optical fibers to be decreased or the diameter of the large-diameter optical fiber to be reduced. The range described above was more preferably from 10 μm to 50 μm.

A third aspect of the present invention is a hollow optical fiber assembly. The hollow optical fiber assembly has small-diameter optical fibers installed between a plastic outer pipe and a plastic inner pipe. The small-diameter optical fibers are plastic optical fibers each comprising a core portion and a cladding portion. The cladding portions are welded to one another.

According to the present invention in this aspect, a large number of small-diameter optical fibers installed in the outer periphery of a large-diameter optical fiber are made of plastic. A core portion, which is an island portion, of a small-diameter optical fiber is constructed of a transparent resin having a high refractive index. An appropriate resin is selected from the group consisting of polystyrene resins, polycarbonate resins, polymethylmethacrylate resins, polyolefin resins, and the like, for example. For a cladding portion, which constitutes a sea portion lying in the periphery surrounding the core portion, a resin having a refractive index lower than that of the core portion is employed. An appropriate resin is selected from the group consisting of polymethylmethacrylate resins, polyolefin resins, fluorine-based resins, and the like, for example. A preferred example of a combination of the core and cladding is, for example, a combination of a polymethylmethacrylate resin and a polystyrene resin. Another preferred example is a combination of a fluorine-based resin and a polymethyl methacrylate resin. When the large-diameter optical fiber is constructed of plastic, it is constructed in a similar manner to the small-diameter optical fibers except that their diameters are different.

A method of manufacturing an all-plastic composite optical fiber in accordance with one embodiment of the present invention in this aspect will now be described with reference to FIGS. 2, 3.

Figure 2:
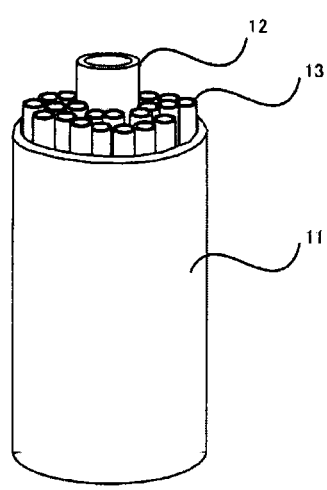
FIG. 2 A process chart for manufacturing the composite optical fiber in accordance with the first embodiment of the present invention.
Figure 3:
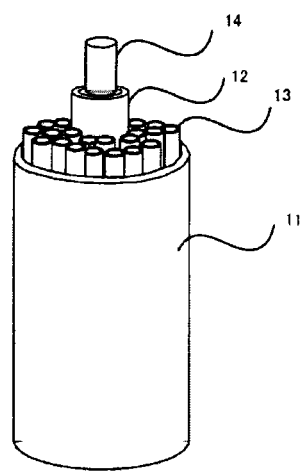
FIG. 3 A process chart for manufacturing the composite optical fiber in accordance with the first embodiment of the present invention.

As shown in FIGS. 2, 3, a plastic outer pipe 11 of a transparent resin and a plastic inner pipe 12 of a transparent resin are concentrically installed. Elemental plastic optical fibers 13 each comprised of a core portion and a cladding portion are inserted between the plastic outer pipe 11 and plastic inner pipe 12 (see FIGS. 2, 3). As can be seen from FIGS. 2, 3, the number of the inserted elemental plastic optical fibers 13 is large. The large number of elemental plastic optical fibers 13 fill up a space between the plastic outer pipe 11 and plastic inner pipe 12. A core rod 14 made of a transparent resin (having a higher refractive index than that of the small-diameter pipe 12) is inserted into the plastic inner pipe 12 (see FIG. 3). The inserted core rod 14 may be a plastic optical fiber preform rod comprised of a core portion and a cladding portion.

The bottom of this base material is heated and subjected to draw processing. During the heating/drawing, air present between the plastic outer pipe 11 and plastic inner pipe 12 is sucked/exhausted. That is, the heating/drawing process is achieved under a reduced-pressure condition. The heating/draw processing causes the cladding portions of the elemental plastic optical fibers 13 to be welded and combined together. During the combination, no void is left in the welded cladding portion because air present among the elemental plastic optical fibers 13 is sucked/exhausted. Consequently, an all-plastic composite optical fiber having a structure shown in FIG. 1 was obtained. The elemental plastic optical fibers 13 are obtained via a melt spinning method. Alternatively, it may be obtained via draw processing.

Now a method of manufacturing a composite optical fiber having a central portion made of inorganic glass in accordance with another embodiment of the present invention will be described with reference to FIG. 2.

As shown in FIG. 2, a plastic outer pipe 11 of a transparent resin and a plastic inner pipe 12 of a transparent resin are concentrically installed. Elemental plastic optical fibers 13 each comprised of a core portion and a cladding portion are inserted between the plastic outer pipe 11 and plastic inner pipe 12 (see FIG. 2). The plastic inner pipe 12 and elemental plastic optical fibers 13 may be inserted at the same time into the large-diameter pipe 11. Alternatively, the small-diameter pipe 12 may be inserted after the elemental plastic optical fibers 13 have been inserted. As can be seen from FIG. 2, the number of the inserted elemental plastic optical fibers 13 is large. The large number of the elemental plastic optical fibers 13 fill up a space between the plastic outer pipe 11 and plastic inner pipe 12. The bottom of this base material in this condition is heated and subjected to draw processing. During the heating/drawing, air between the plastic outer pipe 11 and plastic inner pipe 12 is pulled/exhausted. That is, the heating/draw processing is achieved under a reduced-pressure condition. The heating/draw processing causes the cladding portions of the elemental plastic optical fibers 13 to be welded and combined together. During the combination, no void is left in the welded cladding portion because air present among the elemental plastic optical fibers 13 is pulled/exhausted. Consequently, a hollow optical fiber assembly having a plurality of plastic optical fibers installed in the outer periphery and a hollow central portion was obtained.

Thereafter, the hollow optical fiber assembly was cut to have a desired length, for example, a length of the order of 0.5-5 m. Then, an optical fiber made of inorganic glass such as quartz is inserted into the hollow portion of the hollow optical fiber assembly. Consequently, a composite optical fiber having a central portion constructed of an inorganic glass optical fiber of a type shown in FIG. 4 (or FIG. 5) was obtained. In inserting the inorganic glass optical fiber, a lubricant (such as an oily lubricant, a silicone oil, and a water-based surfactant, for example) is preferably coated on the surface of the inorganic glass optical fiber or alternatively on the inner surface of the small-diameter pipe 12 for the purpose of reducing frictional resistance in insertion. A very small gap might not be completely eliminated between the outer surface of the inorganic glass optical fiber and the inner surface of the hollow plastic image fiber. Accordingly, they are preferably glued together using an epoxy adhesive or the like. They may be glued together all along the longitudinal direction. They may be joined together only at both ends. Such gluing facilitates a cutting process or a polishing process applied to end surfaces.

Figure 6:
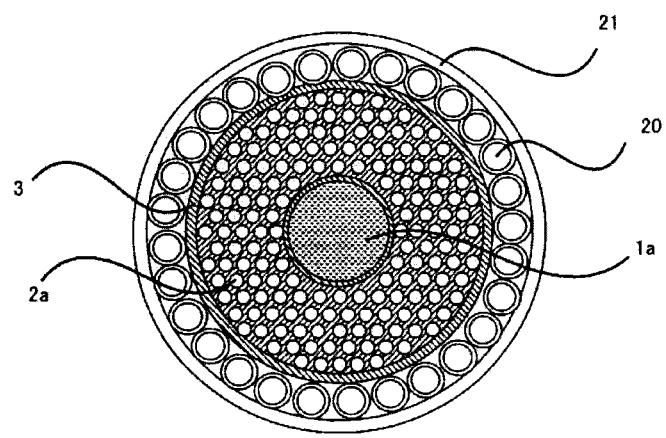
FIG. 6 A cross-sectional view of composite optical fiber in accordance with a fourth embodiment of the present invention.
Figure 7:
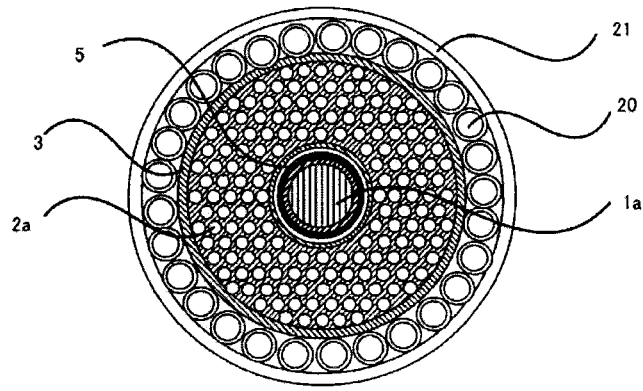
FIG. 7 A cross-sectional view of composite optical fiber in accordance with a fifth embodiment of the present invention.

FIGS. 6 and 7 show an embodiment in which an outer peripheral surface of the composite optical fiber (of the small-diameter optical fibers, or image fibers) is provided with light guiding optical fibers for illumination. The optical fiber of the embodiment shown in a cross-sectional view in FIGS. 6, 7 is employed in, for example, a composite endoscope for medical applications. Its length is 1-5 m, for example. Of course, the length is not limited thereto. The light guiding optical fibers 20 are generally available quartz glass fibers or multi-component glass fibers with a diameter of 30-150 µm. Of course, the fibers are not limited thereto. It should be noted that light guiding optical fibers each having as small a diameter as possible are preferably employed in view of flexural properties. In view of flexural properties, plastic fibers may also be preferably employed in place of the inorganic glass-based fibers. In this case, flexural properties are still good even for fibers each having a diameter larger than that of an inorganic glass-based fiber (30-150 µm), for example, fibers each having a diameter of 50-250 µm.

The light guiding optical fibers 20 are preferably provided on its exterior with an outer jacket 21 for protection. The outer jacket 21 is constructed of a resinous tube (for example, fluorine-based resinous tube, polyurethane-based resinous tube, polyimide-based resinous tube, and the like).

It should be noted that since parts designated by reference numerals in FIGS. 6, 7 similar to those in FIGS. 1, 4, 5 have similar configurations, details thereof are omitted.

Figure 8:
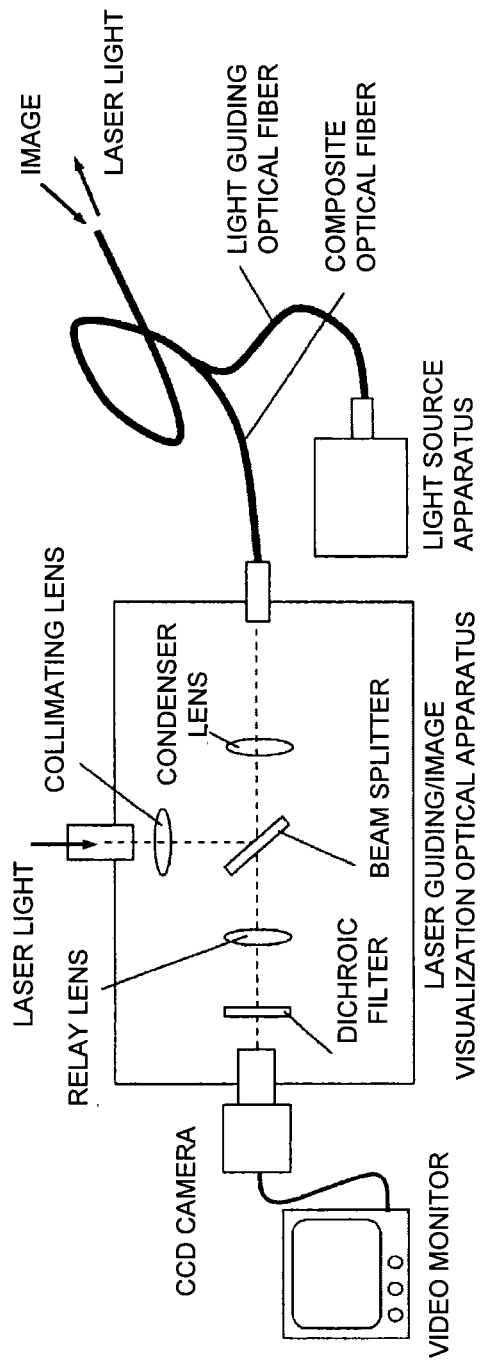
FIG. 8 An explanatory diagram of an endoscope system for laser therapy.

FIG. 8 is an explanatory diagram of a case in which the composite optical fiber of the embodiment described above (for example, FIG. 6) is employed in an endoscope system for laser therapy. In the endoscope system for laser therapy, light illumination, visualization, and laser irradiation are performed at the same time.

The composite optical fiber is divided into two branches on the side of the optical system. The light guiding optical fibers are connected to a light source apparatus as a whole. The composite optical fiber of the other branch is further divided into two sub-branches that are connected to a laser guiding side (large-diameter optical fiber) and an image visualizing side (small-diameter optical fibers).

Image information transmitted through an image fiber portion constituted by the small-diameter optical fibers passes through a condenser lens, a beam splitter, a relay lens, and a dichroic filter for cutting laser light off, and is formed as an image at a CCD camera. Laser light guided from a laser oscillator passes through a collimating lens, the beam splitter, and the condenser lens, and enters a laser light guiding fiber, which is a central portion of the composite optical fiber.

The laser light source is appropriately selected depending upon medical treatments. For example, dye laser, argon ion laser, semiconductor laser, Nd:YAG laser, or Ho:YAG laser is employed as appropriate. Several kinds of laser light sources ranging from visible to near-infrared laser may be employed.

It should be noted that the all-plastic composite fiber described above may be sometimes unsuitable to use for some laser intensity and wavelength. Particularly, when the laser wavelength is near-infrared, a plastic optical fiber having a core of a plastic material that is transparent in a visible-light wavelength range experiences a greater loss in light guiding due to infrared absorption, preventing transmission of near-infrared laser light. In addition, there may be concerns about damage of a laser-entering end surface of the optical fiber. Therefore, an optical fiber having a large-diameter optical fiber made of inorganic glass may be preferable in some cases.

Now explanation will be made hereinbelow with reference to more specific exemplary embodiments.

Embodiment 1

An elemental plastic mono fiber 13 (with a core portion 2a of transparent polystyrene and a cladding portion 2b of transparent polymethylmethacrylate) was drawn via draw processing and cut to have a predetermined length. An inner pipe 12 of transparent polymethylmethacrylate having a small outer diameter was inserted into an outer pipe 11 made of transparent polymethylmethacrylate. The elemental fibers 13 made by the drawing described above were closely packed into a space between the outer pipe 11 and inner pipe 12. A transparent polystyrene core rod 14 was inserted into the central portion of the inner pipe 12. The base material of FIG. 3 was thus constructed.

Air in the whole space inside of the outer pipe 11 was sucked/exhausted to reduce the pressure. Under such a reduced-pressure condition, secondary drawing was performed while heating the tip of the base material. In this way, the all-plastic composite optical fiber having a cross-sectional structure shown in FIG. 1 was obtained. The outer diameter of the all-plastic composite optical fiber was 0.5 mm, the number of pixels (number of small-diameter optical fibers, or number of image fibers) was 8,000, and the diameter of the core portion 1a in the large-diameter optical fiber (laser light guiding fiber) 1 was 135 µm.

The all-plastic composite optical fiber was cut to have a length of 2 m. Both ends were mirror-polished. Thereafter, ten-odd light guiding optical fibers (fibers made of polymethylmethacrylate with a diameter of 125 µm) 20 were installed along the outer periphery of the all-plastic composite optical fiber. The resulting fiber was then inserted into a fluorine-based resinous tube 21 having an outer diameter of 1.0 mm and a thickness of 0.2 mm (see FIG. 6).

One entrance end (rear end) of the fiber was divided into the all-plastic composite optical fiber and light guiding optical fibers. The ends of the branches were connected to an illumination light source apparatus and a laser emission/image visualization optical apparatus, respectively. The tip of the fiber was attached with an objective lens (see FIG. 8).

Illumination light exiting from the light source apparatus was led into the light guiding optical fiber 20 and guided from its tip. The guided light is reflected at an object to be visualized, and an image is formed at the end of the image fibers 2 through the objective lens at the tip. The image light propagated through the image fibers 2 and was led to the laser emission/image visualization optical apparatus. Thereafter, the light passed through the converging lens, beam splitter, relay lens, and dichroic filter, and then was imaged by the CCD camera and displayed on a video monitor.

The laser light source is Nd:YAG laser (KTP). The collimating lens and converging lens shown in FIG. 8 caused laser light of a wavelength of 532 nm to converge. The laser light was led into the laser light guiding portion fiber 1. The laser light propagated through the laser light guiding portion fiber 1 and was guided from the far end.

The fiber thus configured did not break even when it was bent at a bending radius of 5 mm. Moreover, its image properties and laser transmission properties were excellent.

Embodiment 2

The fiber of the embodiment 1 was all-plastic. Fiber of an embodiment 2 below has a large-diameter optical fiber (laser light guiding fiber) 1 made of inorganic glass (quartz glass).

Elemental plastic mono fibers 13 (with a core portion 2a of transparent polystyrene and a cladding portion 2b of transparent polymethylmethacrylate) were drawn via draw processing and cut to have a predetermined length. The elemental fibers 13 made by the primary drawing were closely packed into an outer pipe 11 made of transparent polymethylmethacrylate. An inner pipe 12 having a small outer diameter and made of transparent polymethylmethacrylate was inserted into the central portion of the packed elemental fibers 13. The base material was thus constructed (see FIG. 2).

Air in a gap between the outer pipe 11 and inner pipe 12 was pulled/exhausted to reduce the pressure. Under such a reduced-pressure condition, secondary drawing was performed while heating the tip of the base material. In this way, a hollow optical fiber assembly having a plurality of plastic optical fibers installed in the outer periphery and a hollow central portion was obtained. This product had an outer diameter of 500 μm, a hollow hole with a diameter of 150 μm, and a number of pixels (number of small-diameter optical fibers, or number of image fibers) of 8,000.

Thereafter, the fiber was cut to have a length of 2 m. A quartz optical fiber (having an outer diameter of 125 μm (with a core diameter of 100 μm, a cladding diameter of 120 μm, and a polyimide sheath diameter of 125 μm), and a length of 2.1 m) 1 was inserted into the hollow hole. A low-viscosity two-component epoxy-based adhesive was filled in a gap portion between the hollow optical fiber assembly and quartz fiber at both ends. Thereafter, cure/adhesion was achieved. Finally, the both ends were cut by a diamond saw, and mirror-polished to obtain a composite optical fiber.

The composite optical fiber (having an outer diameter of 0.5 mm (with a center quartz of 125 μm) and a length of 2 m; a central portion made of glass, and a peripheral portion made of plastic) was subjected to a repetitive bending test applied to a central portion of the 2-m length in conditions of [a bending radius of 5 mm, a bend angle of ±135°, and a tensile load of 200 gf]. As a result, the quartz fiber did not break even after 1200 runs (reciprocating). However, part of the plastic image fiber portion lying in the outer periphery fractured. It should be noted that no change was found in light guiding performance of the image fiber portion and quartz fiber after 1,000 times of bending.

As in the embodiment 1, ten-odd light guiding optical fibers 20 were installed along the outer periphery of the composite optical fiber. Thereafter, the resulting fiber was inserted into a fluorine-based resinous tube 21 having an outer diameter of 1.0 mm and a thickness of 0.2 mm (see FIG. 7). Similar processes to the embodiment 1 were then applied, where the ends of the branches were connected to the illumination light source apparatus and laser emission/image visualization optical apparatus, respectively, and the tip of the fiber was attached with an objective lens (see FIG. 8). Moreover, when near-infrared of a wavelength of 1064 nm was employed without converting the wavelength of Nd:YAG laser light, the laser light propagated through the laser light guiding portion fiber 1 and was guided from the far end, without making any damage to the composite optical fiber.

The fiber thus configured did not break even when it was bent at a bending radius of 5 mm. Moreover, its image properties and laser transmission properties were excellent.

The present application claims priority based on Japanese Patent Application No. 2010-131176 filed on Jun. 8, 2010, the disclosure of which is incorporated herein in its entirety.

The invention claimed is:

1. A method of manufacturing a composite optical fiber, the method comprising:
   installing a plurality of elemental plastic optical fibers, each comprising a core portion and a cladding portion, between a plastic outer pipe and a plastic inner pipe,
   installing a core rod, comprising a transparent portion as an optical fiber's constituent element, inside of the plastic inner pipe,
   reducing an air pressure between the plastic outer pipe and the plastic inner pipe, and
   heating and drawing the plastic outer pipe, the elemental plastic optical fibers, the plastic inner pipe, and the core rod, with a gap portion among the plastic outer pipe, the element plastic optical fibers, the plastic inner pipe, and the core rod under a reduced-pressure condition.

2. A method of manufacturing a composite optical fiber, the method comprising:
   installing a core rod, comprising a transparent portion as an optical fiber's constituent element, and elemental plastic optical fibers, each of the elemental plastic optical fibers comprising a core portion and a cladding portion, inside of a plastic pipe, thereby surrounding the core rod with a plurality of the elemental plastic optical fibers,
   reducing an air pressure within the plastic pipe, and
   heating and drawing the plastic pipe, the elemental plastic optical fibers, and the core rod with a gap portion among the plastic pipe, the elemental plastic optical fibers, and the core rod under a reduced-pressure condition.

3. A method of manufacturing a composite optical fiber, the method comprising:
   installing a plurality of elemental plastic optical fibers, each comprising a core portion and a cladding portion, inside of a plastic outer pipe,
   installing a plastic inner pipe to be generally centered within the plastic outer pipe,
   reducing an air pressure between the plastic outer pipe and the plastic inner pipe,
   heating and drawing the plastic outer pipe, the elemental plastic optical fibers, and the plastic inner pipe with a gap portion among the plastic outer pipe, the elemental plastic optical fibers, and the plastic inner pipe under a reduced-pressure condition, and
   installing an optical fiber in the plastic inner pipe after the heating and drawing.

4. The method according to claim 1, wherein the composite optical fiber produced comprises:
   a large-diameter optical fiber and
   small-diameter optical fibers,
   wherein diameters of the small-diameter optical fibers are smaller than a diameter of the large-diameter optical fiber,
   the large-diameter optical fiber is surrounded by the small-diameter optical fibers,
   the small-diameter optical fibers are plastic optical fibers, each of the small diameter optical fibers comprises a core portion and a cladding portion, and
   the small diameter optical fibers have their cladding portions welded to one another.

5. The method according to claim 4,
   wherein the large-diameter optical fiber has a diameter of from 30 μm to 300 μm,
   each of the small-diameter optical fibers comprises a core portion having a diameter of from 1 μm to 10 μm, and the composite optical fiber has an outer diameter of from 0.3 mm to 1.5 mm.

6. The method according to claim 4, wherein a number of the small-diameter optical fibers is from 2,000 to 50,000.

7. The method according to claim 4, wherein the large-diameter optical fiber has a diameter of from 40 μm to 250 μm.

8. The method according to claim 4, wherein a number of the small-diameter optical fibers is from 3,000 to 30,000.

9. The method according to claim 2, wherein the composite optical fiber produced comprises:
a large-diameter optical fiber and
small-diameter optical fibers,
wherein diameters of the small-diameter optical fibers are smaller than a diameter of the large-diameter optical fiber,
the large-diameter optical fiber is surrounded by the small-diameter optical fibers,
the small-diameter optical fibers are plastic optical fibers,
each of the small diameter optical fibers comprises a core portion and a cladding portion, and
the small diameter optical fibers have their cladding portions welded to one another.

10. The method according to claim 3, wherein the composite optical fiber produced comprises:
a large-diameter optical fiber and
small-diameter optical fibers,
wherein diameters of the small-diameter optical fibers are smaller than a diameter of the large-diameter optical fiber,
the large-diameter optical fiber is surrounded by the small-diameter optical fibers,
the small-diameter optical fibers are plastic optical fibers,
each of the small diameter optical fibers comprises a core portion and a cladding portion, and
the small diameter optical fibers have their cladding portions welded to one another.

11. The method according to claim 9, wherein the large-diameter optical fiber has a diameter of from 30 μm to 300 μm,
each of the small-diameter optical fibers comprises a core portion having a diameter of from 1 μm to 10 μm, and
the composite optical fiber has an outer diameter of from 0.3 mm to 1.5 mm.

12. The method according to claim 9, wherein a number of the small-diameter optical fibers is from 2,000 to 50,000.

13. The method according to claim 9, wherein the large-diameter optical fiber has a diameter of from 40 μm to 250 μm.

14. The method according to claim 9, wherein a number of the small-diameter optical fibers is from 3,000 to 30,000.

15. The method according to claim 10, wherein the large-diameter optical fiber has a diameter of from 30 μm to 300 μm,
each of the small-diameter optical fibers comprises a core portion having a diameter of from 1 μm to 10 μm, and
the composite optical fiber has an outer diameter of from 0.3 mm to 1.5 mm.

16. The method according to claim 10, wherein a number of the small-diameter optical fibers is from 2,000 to 50,000.

17. The method according to claim 10, wherein the large-diameter optical fiber has a diameter of from 40 μm to 250 μm.

18. The method according to claim 10, wherein a number of the small-diameter optical fibers is from 3,000 to 30,000.

19. The method according to claim 10, wherein the large-diameter optical fiber comprises inorganic glass.

* * * * *